(12) United States Patent
Keith et al.

(10) Patent No.: US 8,543,342 B1
(45) Date of Patent: Sep. 24, 2013

(54) TOWED ARRAY FLOW NOISE TEST APPARATUS

(75) Inventors: William L. Keith, Ashaway, RI (US); Jeff Dusek, Cambridge, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 441 days.

(21) Appl. No.: 12/894,686

(22) Filed: Sep. 30, 2010

(51) Int. Cl.
*G06F 19/00* (2011.01)

(52) U.S. Cl.
USPC .............................................. 702/48; 367/20

(58) Field of Classification Search
USPC ................................. 367/20, 21, 22
See application file for complete search history.

(56) References Cited

U.S. PATENT DOCUMENTS

| | | | | |
|---|---|---|---|---|
| 3,283,293 A * | 11/1966 | Pavey, Jr. et al. | | 367/172 |
| 3,860,899 A * | 1/1975 | Watlington | | 367/131 |
| RE28,686 E * | 1/1976 | Coulthard | | 73/861.06 |
| 4,011,755 A * | 3/1977 | Pedersen et al. | | 73/861.28 |
| 4,090,168 A * | 5/1978 | Miller et al. | | 367/131 |
| 4,094,193 A * | 6/1978 | Gerlach | | 73/170.29 |
| 4,145,914 A * | 3/1979 | Newman | | 73/290 V |
| 4,160,229 A * | 7/1979 | McGough | | 367/154 |
| 4,202,211 A * | 5/1980 | Perry | | 73/227 |
| 4,232,548 A * | 11/1980 | Baumoel | | 73/861.28 |
| 4,333,169 A * | 6/1982 | Hoyt | | 367/1 |
| 4,388,711 A * | 6/1983 | Fay | | 367/135 |
| 4,554,650 A * | 11/1985 | Brown et al. | | 367/154 |
| 4,660,183 A * | 4/1987 | McGowan et al. | | 367/15 |
| 4,679,179 A * | 7/1987 | Lally | | 367/162 |
| 4,732,045 A * | 3/1988 | Blackburn | | 73/801 |
| 4,984,218 A * | 1/1991 | Ritter et al. | | 367/15 |
| 5,010,525 A * | 4/1991 | Skinner et al. | | 367/13 |
| 5,251,183 A * | 10/1993 | McConnell et al. | | 367/21 |
| 5,251,469 A * | 10/1993 | Chan | | 73/1.86 |
| 5,381,382 A * | 1/1995 | Marschall | | 367/20 |
| 5,384,752 A * | 1/1995 | Duren et al. | | 367/38 |
| 5,477,506 A * | 12/1995 | Allen | | 367/140 |
| 5,521,885 A * | 5/1996 | Harvey | | 367/154 |
| 5,528,555 A * | 6/1996 | Santos et al. | | 367/22 |
| 5,532,979 A * | 7/1996 | Hansen et al. | | 367/106 |
| 5,646,470 A * | 7/1997 | de Groot | | 310/337 |
| 5,680,371 A * | 10/1997 | Miklovic | | 367/123 |
| 5,789,844 A * | 8/1998 | de Groot | | 310/329 |
| 5,822,276 A * | 10/1998 | Miklovic | | 367/103 |
| 5,844,860 A * | 12/1998 | Miller | | 367/154 |
| 6,058,072 A * | 5/2000 | Abraham | | 367/20 |
| 6,119,070 A * | 9/2000 | Beneteau et al. | | 702/45 |
| 6,160,761 A * | 12/2000 | Sansone | | 367/149 |
| 6,185,154 B1 * | 2/2001 | Miller | | 367/130 |
| 6,292,436 B1 * | 9/2001 | Rau et al. | | 367/149 |
| 6,473,365 B2 * | 10/2002 | Joh et al. | | 367/154 |
| 6,684,160 B1 * | 1/2004 | Ozbek et al. | | 702/17 |
| 7,040,158 B1 * | 5/2006 | Keith et al. | | 73/170.33 |

(Continued)

*Primary Examiner* — Jonathan C Teixeira Moffat
*Assistant Examiner* — Alvaro Fortich
(74) *Attorney, Agent, or Firm* — James M. Kasischke; Michael P. Stanley (57) ABSTRACT

An apparatus is provided to directly measure the flow noise characteristics of both acoustic sensors and accelerometers mounted in a towed array hose. Sensors can be mounted in a full-scale diameter array module test apparatus and can be subjected to high Reynolds number flow fields that have the physical features of at-sea towing conditions. Additionally, rapid re-design of sensor mountings, hose materials, and actual sensors can be accomplished and evaluated. The parameters of internal tension and flow speed can vary independently in order to determine their importance.

3 Claims, 5 Drawing Sheets

(56) References Cited

U.S. PATENT DOCUMENTS

| | | | |
|---|---|---|---|
| 7,069,950 B1* | 7/2006 | Bittner | 137/625.37 |
| 7,130,242 B1* | 10/2006 | Keith et al. | 367/20 |
| 7,206,258 B1* | 4/2007 | Fisher et al. | 367/141 |
| 7,295,013 B2* | 11/2007 | Conti et al. | 324/350 |
| 7,379,386 B2* | 5/2008 | Muyzert et al. | 367/63 |
| 7,466,625 B2* | 12/2008 | Robertsson et al. | 367/24 |
| 7,599,253 B1* | 10/2009 | Huang | 367/130 |
| 7,646,669 B1* | 1/2010 | Stevenson | 367/13 |
| 7,782,712 B2* | 8/2010 | Keith et al. | 367/154 |
| 7,881,156 B2* | 2/2011 | Keith et al. | 367/130 |
| 8,270,255 B2* | 9/2012 | Cuschieri et al. | 367/154 |
| 8,300,497 B1* | 10/2012 | Keith et al. | 367/20 |
| 2003/0005872 A1* | 1/2003 | DePoy, II | 114/21.3 |
| 2003/0167125 A1* | 9/2003 | Seemann et al. | 702/2 |
| 2005/0249040 A1* | 11/2005 | Luc et al. | 367/178 |
| 2006/0215493 A1* | 9/2006 | Sullivan | 367/126 |
| 2008/0198695 A1* | 8/2008 | Abdi | 367/134 |
| 2008/0219095 A1* | 9/2008 | Perciot et al. | 367/24 |
| 2009/0296521 A1* | 12/2009 | Perciot et al. | 367/24 |
| 2009/0299661 A1* | 12/2009 | Green et al. | 702/54 |
| 2010/0039889 A1* | 2/2010 | Teigen et al. | 367/20 |
| 2012/0087207 A1* | 4/2012 | Kostov et al. | 367/20 |
| 2012/0113757 A1* | 5/2012 | Kurpiewski | 367/173 |

\* cited by examiner

TOWED ARRAY FLOW NOISE TEST APPARATUS

STATEMENT OF GOVERNMENT INTEREST

The invention described herein may be manufactured and used by or for the Government of the United States of America for Governmental purposes without the payment of any royalties thereon or therefor.

CROSS REFERENCE TO OTHER PATENT APPLICATIONS

None.

BACKGROUND OF THE INVENTION

1. Field of the Invention

The invention generally relates to acoustic system testing devices and particularly to a towed array testing apparatus.

2. Description of the Prior Art

Flow noise in towed arrays results from convective energy due to turbulent wall pressure fluctuations on the surface of the array, and flow-induced vibrations of the array. Standard towed array designs are aimed at filtering convective energy using a combination of hydrophone size, hydrophone grouping as well as the stand-off distance between the hydrophone and the hosewall of the array.

Recent measurements made using experimental towed arrays, described by Keith and Cipolla ("Spectral Features of Wall Pressure Fluctuations Measured with an Experimental Towed Array," NUWC TR 11,805, 26 March, 2007); Cipolla and Keith ("Measurements of the Wall Pressure Spectra on a Full Scale Experimental Towed Array," Ocean Engineering, Vol. 35, Issue 10, July 2008, pp. 1052-1059); and Keith et al. ("Drag and Wall Pressure Measurements on a Towed Array Model at High Reynolds Numbers," NUWC TR 11,855, Feb. 11, 2008) have shown the existence of low frequency spectral energy which extends across all measured wavenumbers.

Presently, the physics of this energy is not well understood. Comparison of the results presented by Cipolla and Keith and Keith et al. indicate that internal tension in the towed array may have a significant effect on these low frequency spectral levels. The complexity of the turbulent boundary layer wall pressure fluctuations and related fluid/structure interactions extremely limits purely analytical or computational approaches.

Full scale experimental efforts are very costly and time consuming. Laboratory testing which can provide results directly relevant to full scale arrays, and allow design parameters to be varied, are therefore very valuable.

Also known in the prior art is Keith et al., U.S. Pat. No. 7,130,242 B1, which is said to disclose a system and method for detecting an acoustic signal in the presence of flow noise produced by the turbulent flow field that develops about a hosewall of a towed array. Pressure is sensed with pressure sensors at two diametrically-opposed locations at the surface of the hosewall over a period of time. The sensed pressure signals are used to generate an ensemble-averaged cross-spectra which effectively cancels out the flow noise while retaining the acoustic signal associated with a possible target of interest.

Also known in the prior art is Keith et al., United States Patent Application Publication No. 20090303837, which is said to disclose a towed array having hot-film sensors and anemometer circuitry to calculate the angle of inclination of the towed array in real time during deployment of the towed array in a sea water environment. The hot-film sensors are arranged in pairs along the length of the towed array to increase the sensitivity of the inclination angle determinations and are located flush with an exterior surface of the towed array. The pairs of hot-film sensors determine the local sheer stresses on the towed array, and these measurements are converted to inclination angles using an empirically derived look-up table.

Based on existing knowledge of the prior art, there exists a need for convenient, inexpensive and rapid systems and methods for examining designs of towed arrays so as to provide towed array configurations that exhibit improved operational properties.

SUMMARY OF THE INVENTION

A primary objective and general purpose of the present invention is to provide a towed array flow noise test apparatus.

It is a further objective of the present invention to provide a towed array flow noise test apparatus operable over a flow velocity range of 1 meter per second to 15.5 meters per second.

It is a still further objective of the present invention to provide a towed array flow noise test apparatus that can control an applied tension independent of other parameters.

It is a still further objective of the present invention to provide a towed array flow noise test apparatus that can test sensors selected from the group consisting of acoustic sensors, pressure sensors, fleet hydrophones and accelerometers.

It is a still further objective of the present invention to provide a towed array flow noise test apparatus that can directly measure a wavenumber-frequency spectrum.

It is a still further objective of the present invention to provide a towed array flow noise test apparatus in which a hose module is configured to respond to a turbulent wall pressure, a mean wall shear stress, and a turbulent wall shear stress.

It is a still further objective of the present invention to provide a towed array flow noise test system having a towed array flow noise test apparatus and a general purpose programmable computer programmed with instructions recorded on a machine readable medium.

Accordingly, the present invention features a towed array flow noise test apparatus operable with a water flow test facility having a main flow channel. The towed array flow noise test apparatus comprises an enclosure fixed adjacent a main flow channel of a water flow test facility. The water flow test facility has an aperture defined in a wall thereof, with the enclosure being in fluid communication with a flow in the main flow channel via the aperture. When the flow is fixed adjacent to the main flow channel; there is a flow velocity.

A hose module situated within the enclosure. The hose module has one end held in fixed relation to an end of the enclosure and another end in communication with a proximal end of a tensioning apparatus.

The tensioning apparatus comprises a load cell with the tensioning apparatus having a distal end in fixed relation to another end of the enclosure. The tensioning apparatus is configured to apply a tension to the hose module and at least one sensor situated within the hose module. The sensor has one or more sensor output terminals configured to provide a signal representative of a value measured by the sensor.

In one embodiment, the tensioning apparatus is a turnbuckle and in another embodiment, the hose module comprises urethane. In yet another embodiment, the test apparatus is configured to respond to changes in the flow velocity in the primary test section within the range of 1 meter to 15.5 meters per second.

In a further embodiment, the sensor is at least eight sensors and the test apparatus is configured to provide a direct measurement of a wavenumber-frequency spectrum.

In still another embodiment, the test apparatus is configured to control the applied tension independently of the flow velocity in the primary test section.

In an additional embodiment, the hose module is configured to respond to a turbulent wall pressure, a mean wall shear stress, and a turbulent wall shear stress.

In one more embodiment, there is provided a system comprising a towed array flow noise test apparatus and a general purpose programmable computer programmed with instructions recorded on a machine readable medium. The general purpose programmable computer is configured by instruction to receive the signal representative of a value measured by the sensor. The general purpose programmable computer is also configured to: compute a result; record the result, display the result or transmit the result to another computational device.

In yet a further embodiment, the result is at least one of a temporal and a spatial statistical feature of a flow noise.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION OF THE INVENTION

The inventors have identified the need to make direct measurements of the flow noise characteristics of various sensors subjected to the excitation of a turbulent boundary layer in order to assess the properties of different sensor designs and configurations.

The invention provides a tool, namely an apparatus or a fixture to allow the flow noise characteristics of both traditional acoustic sensors and also accelerometers mounted in a towed array hose to be measured directly. Such sensors can be mounted in a full-scale diameter array module test apparatus and can be subjected to high Reynolds number flow fields that have the dominant physical features of at—sea towing conditions.

Additionally, rapid re-design of sensor mountings, hose materials, and actual sensors can be accomplished and evaluated. The parameters of internal tension and flow speed can be varied independently in order to determine their relative importance. In addition to existing sensor designs, new high-risk sensor designs can be tested quickly and at low cost.

Apparatus Design

Figure 1:
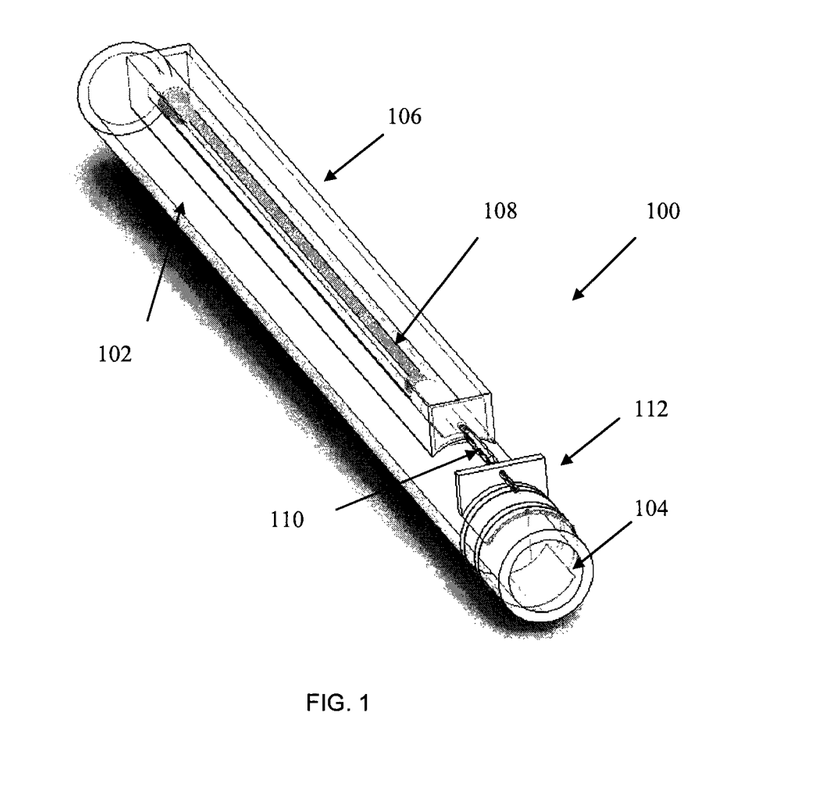
FIG. 1 is an illustration of a preferred embodiment of a test apparatus assembly according to principles of the present invention.
Figure 2:
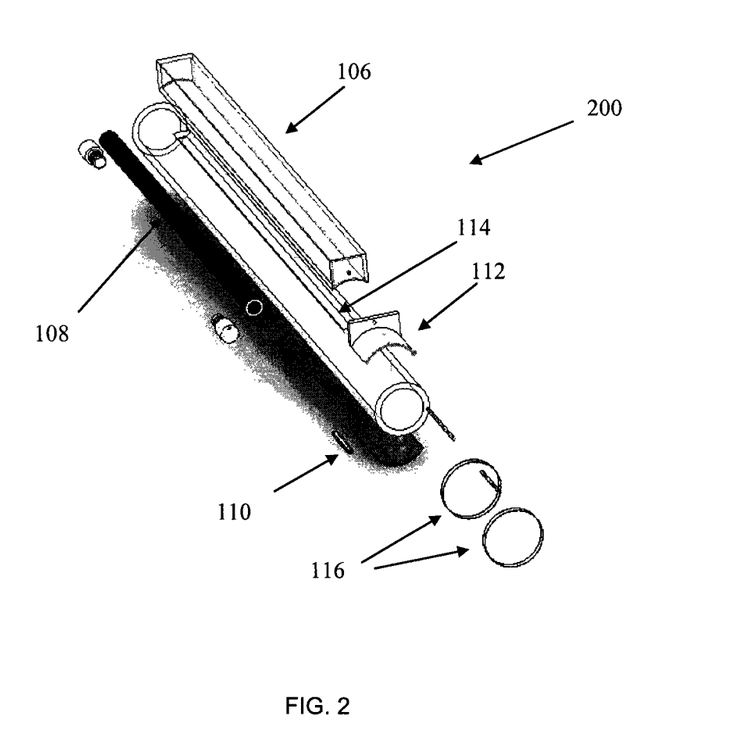
FIG. 2 is an illustration in exploded view of the test apparatus depicted in FIG. 1.

In a preferred embodiment, a section of acrylic tubing defines the primary test section, as shown in FIG. 1 and in FIG. 2 in an exploded view. It is believed that this basic test apparatus design can be used in any hydrodynamic pipe flow facility.

Turning to FIG. 1 and according to the design of a preferred embodiment 100, there is illustrated a circular test section 102 of a quiet water tunnel facility. The circular test section 102 can be made from acrylic tubing. A fully developed turbulent pipe flow 104 of water at high Reynolds number passes through the quiet water tunnel facility.

A 'wetbox' (also referred to herein as the wetbox 106) is provided to contain a hose module 108, which in a preferred embodiment is made from urethane. In other embodiments, other materials of construction can be used for the hose module 108.

A wetbox is an enclosure that is configured to contain a hose module having sensors mounted therein. The wetbox provides a fluid communication with the fluid flow in a primary test section of a quiet water tunnel facility so that the hose module is effectively within the flow regime that is obtained in the primary test section.

In a preferred embodiment, the wetbox 106 can be constructed from an acrylic material. In other embodiments, other materials can be used for the wetbox.

The urethane hose module 108 contains acoustic or nonacoustic sensors, as described hereinbelow. A tensioning apparatus, such as a turnbuckle 110, is provided between one end of the hose module 108 and a fixing point 112 on the circular test section, which is in fixed relation to an end of the wetbox 106. The other end of the hose module 108 is held in fixed location relative to the wetbox 106. The turnbuckle 110 allows tension in the hose module 108 to be adjusted as an independently variable parameter.

Turning now to FIG. 2, according to the design of a preferred embodiment, the apparatus of FIG. 1 is shown in an exploded view 200. Channel 114 is defined in the acrylic tubing 102 to provide fluid communication with the wetbox 106 in which the hose module 108 is situated. Different hose modules and sensor mounting configurations can be tested in the apparatus. Inexpensive and readily—available parts such as turnbuckles 110 and hose clamps 116 can be used to assemble the apparatus.

Figure 3:
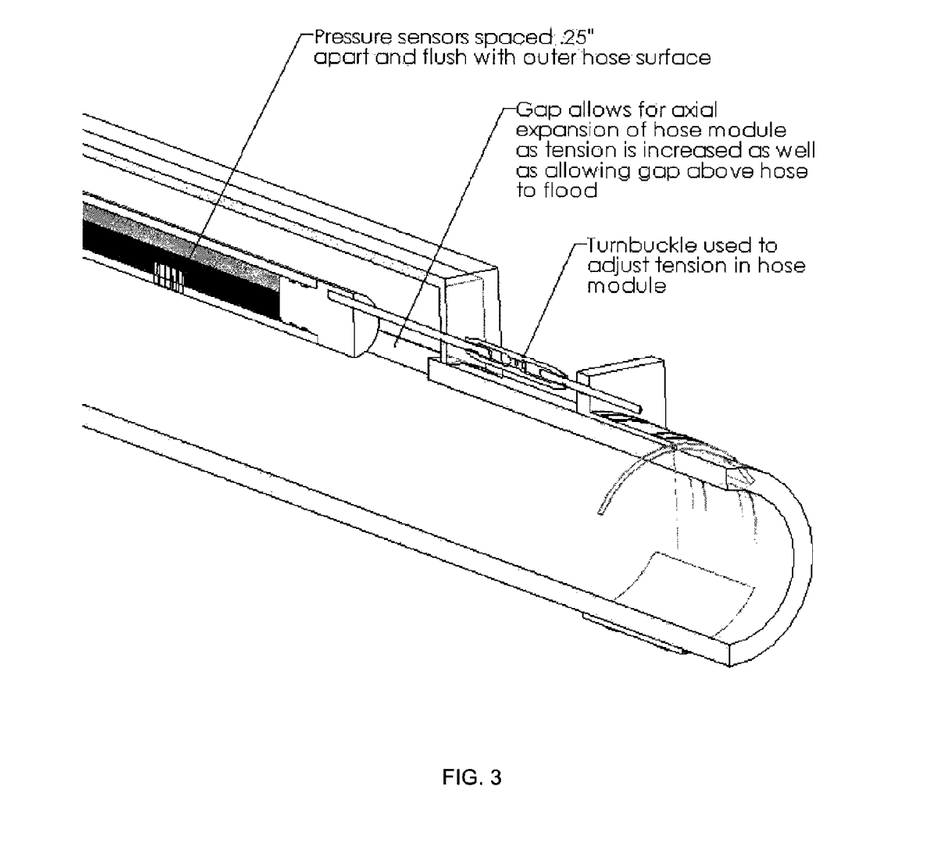
FIG. 3 is an illustration in cut-away view of the test apparatus of FIG. 1 configured with wall pressure sensors.

The purpose of the channel 114 is to allow a portion of the hose module 108 to be exposed to the turbulent pipe flow. According to the design, the hose module 108 is enclosed in the wetbox 106 which is expected to be flooded through a small slot at the downstream end of the cut channel, as shown in FIG. 3.

The static pressure within the wetbox 106 is expected to be the same as that in the turbulent pipe flow at the test apparatus location. This is expected to eliminate any lift force on the array hose section. A fairing piece is expected to be employed at the up-stream end of the hose module in order to minimize flow disturbances. At the downstream end of the apparatus, a threaded rod is expected to exit from the wetbox 106 and to attach to a turnbuckle 110, which is expected to be used to vary the tension in the hose module 108, as shown in FIG. 1.

Figure 4:
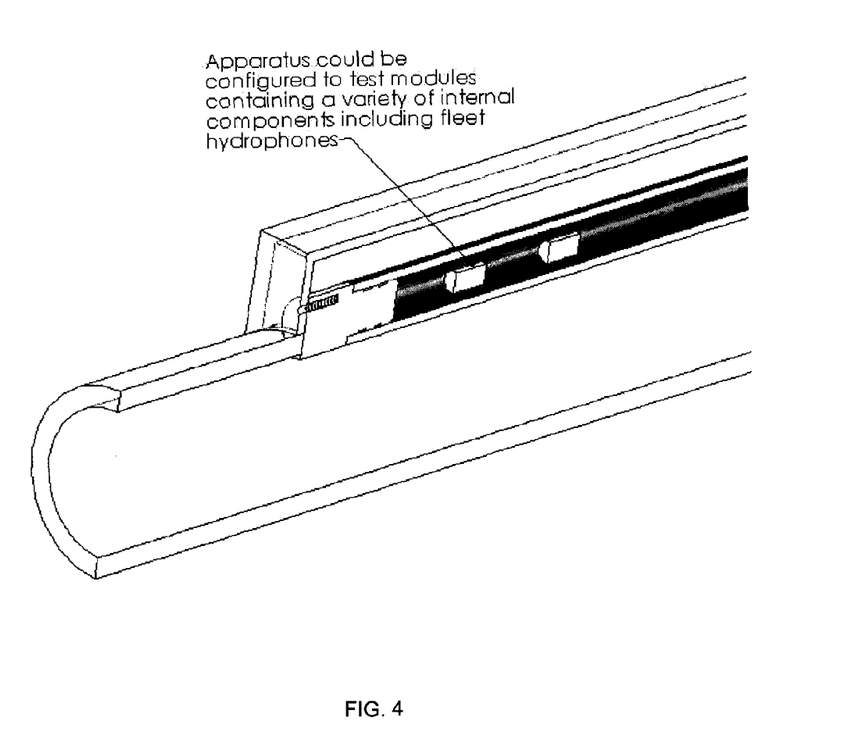
FIG. 4 is an illustration in cut-away view of the test apparatus of FIG. 1 configured with conventional hydrophones.

A load cell is expected to be employed to measure the tension exerted by the turnbuckle 110. The load cell has at least one output terminal configured to provide a signal representative of the tension applied. Wall pressure sensors, hydrophones, and accelerometers can be mounted within each hose test module as shown in FIG. 3 and FIG. 4.

The apparatus provides a facility for real-time collection of array sensor data. Different hose material and different hose wall thicknesses can be evaluated. The static pressure in the turbulent pipe flow can be independently controlled in the flow facility and the pressure within the array hose can be independently set (nominally at 10 psi) prior to installation.

Direct measurements of the flow-induced pressure fluctuations are expected to be obtained from the sensor output signals provided at sensor output terminals. In some embodiments, the sensor output signals are voltage signals. In other embodiments, the sensor output signals are current signals. The sensor output terminals are in electrical communication with equipment that provides real time data logging, data analysis, data recording and display capabilities.

In a preferred embodiment, the real time data logging and data analysis equipment is based on a general purpose programmable computer operating under the control of instructions recorded on a machine readable medium (for example: software, firmware, or hard-wired instructions). The autospectra and cross-spectra between sensors are expected to be measured to determine the temporal and spatial statistical features of the flow noise.

In one preferred embodiment, if eight or more equally spaced sensors (of one type) are mounted in the test hose, a direct measurement of the wavenumber-frequency spectra can be made. The velocity in the test section is expected to be varied significantly (by a factor of ten or greater) to evaluate the effect of the flow velocity parameter—independent of the tension in the hose or the static pressure.

An advantage of the apparatus is the rapid and inexpensive manner in which tests can be made on a wide variety of sensors and mounting configurations. The apparatus allows tension in the hose to be varied independent of the free-stream velocity (which is analogous to tow speed). This is a condition that cannot be achieved in at-sea towing.

Additionally, the quiet water tunnel allows free-stream velocities in a range from speeds as low as two knots (1 m/s) to thirty knots (15.5 m/s) and higher to be achieved.

Because the excitation of the array test apparatus is from fully-developed turbulent pipe flow; the mean wall shear stress can be directly determined from the static pressure drop along the pipe.

During tow tests, it is difficult to determine the local mean wall shear stress due to the small viscous sublayers within the boundary layers, and other physical constraints. It is also difficult to measure the boundary thickness during tow tests.

In the apparatus according to principles of the invention, the boundary thickness is by definition the internal pipe radius. Boundary layer thickness and mean wall shear stress are primary scaling parameters for wall pressure spectra and wall shear stress spectra. Note that for the purposes of this type of flow noise testing, the differences between an external turbulent boundary layer and internal pipe flow boundary layer can be accounted for. However, the actual boundary layer thickness at-sea is greater than a typical pipe radius, such that scaling laws must be invoked. Such laws are well established, as discussed by Keith et al. ("Drag and Wall Pressure Measurements on a Towed Array Model at High Reynolds Numbers," NUWC TR 11,855, Feb. 11, 2008).

The test apparatus is designed to allow the array hose to respond to the turbulent wall pressure, mean wall shear stress, and turbulent wall shear stress, in a manner consistent with an at-sea configuration. Since the hosewall interface with the turbulent boundary layer extends over only a portion of the hosewall circumference, the sensor response may be less than the at-sea condition, depending on the type of sensors being used. For example, this effect is not expected to influence the wall pressure sensors shown in FIG. 3, but is expected to influence the conventional type hydrophones shown in FIG. 4. An empirical correction can be applied to account for this effect.

Standoff distance and sensor size are the two primary mechanisms by which towed arrays filter flow noise. The effect of stand-off distance between the conventional hydrophones and fluid/solid interface can be directly determined by changing the mounting configuration or sensor size. Improvements in these filtering mechanisms are expected to lead to significant self—noise improvements.

Alternatives to the quiet water tunnel test apparatus include sea trials, lake tests, tow tank testing, and numerical modeling. Sea trials, lake tests, and tow tank tests are costly, time-consuming, and limit the parameters (such as the mean wall shear stress and boundary layer thickness) which can be varied independently and measured.

Current computational fluid dynamics codes are limited to Reynolds number two orders of magnitude lower than operational conditions. Additionally, the present disclosure focuses on the complicated coupled response of the sensors and array internal structure to excitation by a turbulent boundary layer. Currently, linking finite element modeling and computation fluid dynamics codes are not feasible to obtain the desired results. Results obtained from the test apparatus are expected to provide useful data for ongoing computational efforts.

Figure 5:
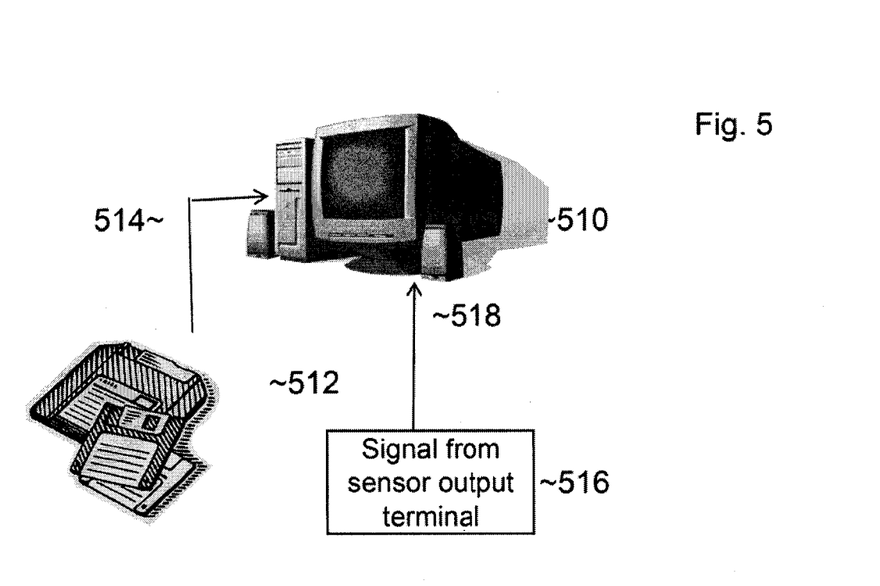
FIG. 5 is a diagram showing a programmable general purpose computer programmed with a set of instructions on a machine-readable medium, which instructions when operating control the programmable general purpose computer to accept data, to analyze the data, and to report or display the results of the analysis.

FIG. 5 is a schematic diagram that illustrates a hardware system that can be provided to implement the disclosed invention. As illustrated in the figure, the system includes a general purpose programmable computer 510 programmed with computer instructions in a machine-readable format (e.g., software) on a machine-readable medium such as a floppy disk 512 (e.g., software). Arrow 514 indicates that the floppy disk 512 can be inserted into a disk drive of the computer. The computer 510 is configured to receive the required digital data, for example from sensing hardware 516 (for example: one or more hydrophones).

Arrow 518 indicates the flow of data from the sensing hardware 516 to the computer 510. The computer 510, when running the software, is configured to: perform the requisite calculations; provide a computed result in a convenient form, such as a graphical display or a numerical table; record the result (for example: on a floppy 512); store the result for later use; transmit the result to a user or to another computational system; and/or display the result to a user (for example: on the display of the computer 510).

Flow Chart

Figure 6:
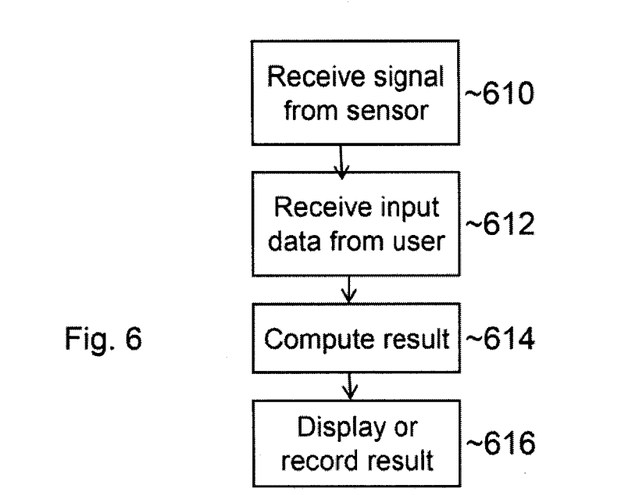
FIG. 6 is a schematic flow diagram of the process of obtaining data and computing a result.

FIG. 6 is a schematic flow diagram of the process of obtaining data and computing a result. The process involves the step of collecting data from at least one sensor, as expressed in box 610.

The process involves the step of accepting input data from a user, as expressed in box 612. The input data provided by the user can include test conditions, such as an applied tension, or a flow rate or flow condition. The process involves the step of computing a result, as expressed in box 614.

The process also involves the step of recording, storing and/or displaying the result, as expressed in box 616.

DEFINITIONS

Recording the results from a data acquisition (for example: recording results at a particular wavelength, frequency or wave-number) is understood to mean a writing output data to a storage element, to a machine-readable storage medium, or to a storage device.

Machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media.

As is known to those of skill in the machine-readable storage media arts, new media and formats for data storage are continually being devised, and any convenient, commercially-available storage medium and corresponding read/write device that may become available is likely to be appropriate for use; especially if it provides any of a greater storage capacity, a higher access speed, a smaller size, and a lower cost per bit of stored information. Well-known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two-dimensional bar codes. Recording image data for later use (for example: writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing data to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including a data processing algorithm coded as "firmware" can reside in memory physically inside of a microcomputer chip or in memory external to the microcomputer or in a combination of internal and external memory. Similarly, analog signals can be digitized by a stand alone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard.

The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer.

The computer can run any one of a variety of operating systems, such as for example, any one of several versions of Windows, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example: hard-wired logic), in software (for example: logic encoded in a program operating on a general purpose processor), and in firmware (for example, logic encoded in a non-volatile memory that is invoked for operation on a processor as required).

The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein.

THEORETICAL DISCUSSION

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A towed array flow noise test apparatus operable with a water flow test facility having a circular main flow channel with an aperture defined in a longitudinal wall thereof, said apparatus comprising:
    an enclosure longitudinally adjacent the circular main flow channel and in fluid communication with a flow having a flow velocity in the main flow channel via the aperture;
    a tensioning apparatus comprising a load cell with said tensioning apparatus having a distal end in fixed relation to a first end of said enclosure;
    a hose module faired within said enclosure, said hose module having one end held in fixed relation to a second end of said enclosure, and a second end of said hose module in communication with a proximal end of said tensioning apparatus, said tensioning apparatus configured to apply a tension to said hose module; and
    at least one sensor situated within said hose module, said at least one sensor having at least one sensor output terminal configured to provide a signal representative of a value measured by said sensor;
    wherein said test apparatus is configured to provide outputs from the sensors while changes in the flow velocity in the main channel vary from 1 meter per second to 15.5 meters per second;
    wherein said apparatus is configured to control the applied tension independently of the flow velocity in the main channel.

2. The towed array flow noise test apparatus of claim 1, wherein said at least one sensor is at least eight sensors, and said test apparatus is configured to provide a direct measurement of a wavenumber-frequency spectrum.

3. The towed array flow noise test apparatus of claim 1, wherein said hose module is configured to respond to a turbulent wall pressure, a mean wall shear stress, and a turbulent wall shear stress.

* * * * *